US009381108B2

(12) United States Patent
Longoni et al.

(10) Patent No.: US 9,381,108 B2
(45) Date of Patent: Jul. 5, 2016

(54) DEVICE FOR THE ANALYSIS OF URINE

(75) Inventors: Giovanni Longoni, Bovisio Masciago (IT); Renzo Orsenigo, Carate Brianza (IT)

(73) Assignee: REDOAK S.R.L., Milan (IT)

( * ) Notice: Subject to any disclaimer, the term of this patent is extended or adjusted under 35 U.S.C. 154(b) by 620 days.

(21) Appl. No.: 12/736,539

(22) PCT Filed: Mar. 23, 2009

(86) PCT No.: PCT/IB2009/000584
§ 371 (c)(1),
(2), (4) Date: Dec. 16, 2010

(87) PCT Pub. No.: WO2009/127925
PCT Pub. Date: Oct. 22, 2009

(65) Prior Publication Data
US 2011/0092786 A1    Apr. 21, 2011

(30) Foreign Application Priority Data

Apr. 17, 2008  (IT) .............................. MI2008A0711

(51) Int. Cl.
*A61M 1/00* (2006.01)
*A61F 5/453* (2006.01)
*A61B 5/145* (2006.01)
*A61B 5/20* (2006.01)
*A61B 5/00* (2006.01)

(52) U.S. Cl.
CPC ............. *A61F 5/453* (2013.01); *A61B 5/14507* (2013.01); *A61B 5/20* (2013.01); *A61B 5/201* (2013.01)

(58) Field of Classification Search
None
See application file for complete search history.

(56) References Cited

U.S. PATENT DOCUMENTS

| 4,314,484 | A  | * | 2/1982  | Bowman ..................... 73/861.41 |
| 4,334,537 | A  | * | 6/1982  | Peterson ....................... 604/327 |
| 5,616,138 | A  | * | 4/1997  | Propp ........................... 604/317 |
| 6,464,848 | B1 | * | 10/2002 | Matsumoto .............. 204/403.06 |
| 2006/0100743 | A1 | * | 5/2006  | Townsend et al. ............. 700/266 |
| 2008/0312550 | A1 | * | 12/2008 | Nishtala et al. ............... 600/549 |
| 2010/0121220 | A1 | * | 5/2010  | Nishtala ........................ 600/581 |
| 2010/0286559 | A1 | * | 11/2010 | Paz et al. ....................... 600/581 |

FOREIGN PATENT DOCUMENTS

WO    WO2007005851    11/2007

* cited by examiner

*Primary Examiner* — Etsub Berhanu
*Assistant Examiner* — Karen Toth
(74) *Attorney, Agent, or Firm* — R. Ruschena Patent Agent, LLC

(57) ABSTRACT

A device for the analysis of urine designed to be connected in series to a catheter (12) of a patient's urine, comprises: means (14) for analyzing a sample of urine, means (13, 19) for feeding a pre-established quantity of urine coming from the catheter to said analysis means, and automatic control means (21) for controlling the feeding of the pre-established quantity of urine to the analysis means through said means for feeding, and for activating the analysis of the urine through said urine analysis means when the pre-established quantity of urine is supplied thereto.

12 Claims, 3 Drawing Sheets

DEVICE FOR THE ANALYSIS OF URINE

RELATED APPLICATIONS

This is a U.S. National Stage application according to 35 U.S.C. 371 of PCT/IB2009/00584 application filed on Apr. 17, 2008.

BACKGROUND OF THE INVENTION

1. Field of the Invention

The present invention relates to an automatic device for the analysis of a patient's urine, suitable for being applied in series to the catheter of the patient's urine to continuously monitor the renal activity of the patient.

2. Brief Description of the Prior Art

The production of devices for the chemical analysis of urine, equipped with electrochemical measuring cells, is known in the art. These devices are positioned in specific analysis laboratories of the hospital and effect the desired measurements (for example pH, sodium, potassium, chloride and ammonium ions) on a sample taken manually by a health worker. Before being analyzed, the sample is diluted and is then introduced into the electrochemical measurement cell.

This procedure can be laborious and requires the intervention of the health worker whenever a chemical analysis of the patient is required. The main difficulties are: the impossibility of continuously monitoring the urine as soon as it is produced, as can be important in the case of serious patients or intensive-care patients;

- the risk deriving from transporting the sample taken from the patient to the analysis laboratory;
- the necessity of having a constant availability of the analysis laboratory for effecting clinical chemical analyses with the necessary frequency.

The use of devices in series with the catheter of the patient's urine, suitable for measuring the volume of urine produced over a time period, is also known. These known devices comprise a system for dividing the urine into drops and a sensor capable of counting the drops formed; these types of apparatuses, however, are not capable of effecting a clinical chemical analysis of the urine, and consequently a manual sampling must be taken (for example from a discharge container of the device), in addition to the dilution of the sample taken for subsequent analysis in the electrochemical measurement cell.

SUMMARY OF THE INVENTION

The general objective of the present invention is to overcome the above drawbacks by providing an analysis device of urine which allows the physical-chemical characteristics of the urine produced by the patient to be automatically and continuously monitored.

A further objective of the invention is to perform the monitoring described above in a simple and convenient way, without the necessity of laborious interventions on the part of a health worker.

Another objective of the invention is to provide a device for the analysis of urine which is compact and can be arranged near the patient's bed without creating encumbrances.

Yet another objective of the invention is to provide an analysis device which also allows the quantity of urine produced over a period of time by the patient, to be monitored.

In view of this objective, a device for the analysis of urine has been conceived, according to the invention, destined for being connected in series to a catheter of a patient's urine, the device comprising:

- means for analyzing a sample of urine,
- means for feeding a pre-established quantity of urine coming from the catheter to said analysis means, and
- automatic control means for controlling the feeding of the pre-established quantity of urine to the analysis means through said means for feeding, and for effecting the analysis of the urine through said urine analysis means when the pre-established quantity of urine is supplied thereto.

BRIEF DESCRIPTION OF THE DRAWINGS

To clarify the explanation of the innovative principles of the present invention and its advantages with respect to the known art a possible embodiment applying these principles is described hereunder with the help of the enclosed drawings. In the drawings.

DETAILED DESCRIPTION OF THE PREFERRED EMBODIMENT

Figure 1:
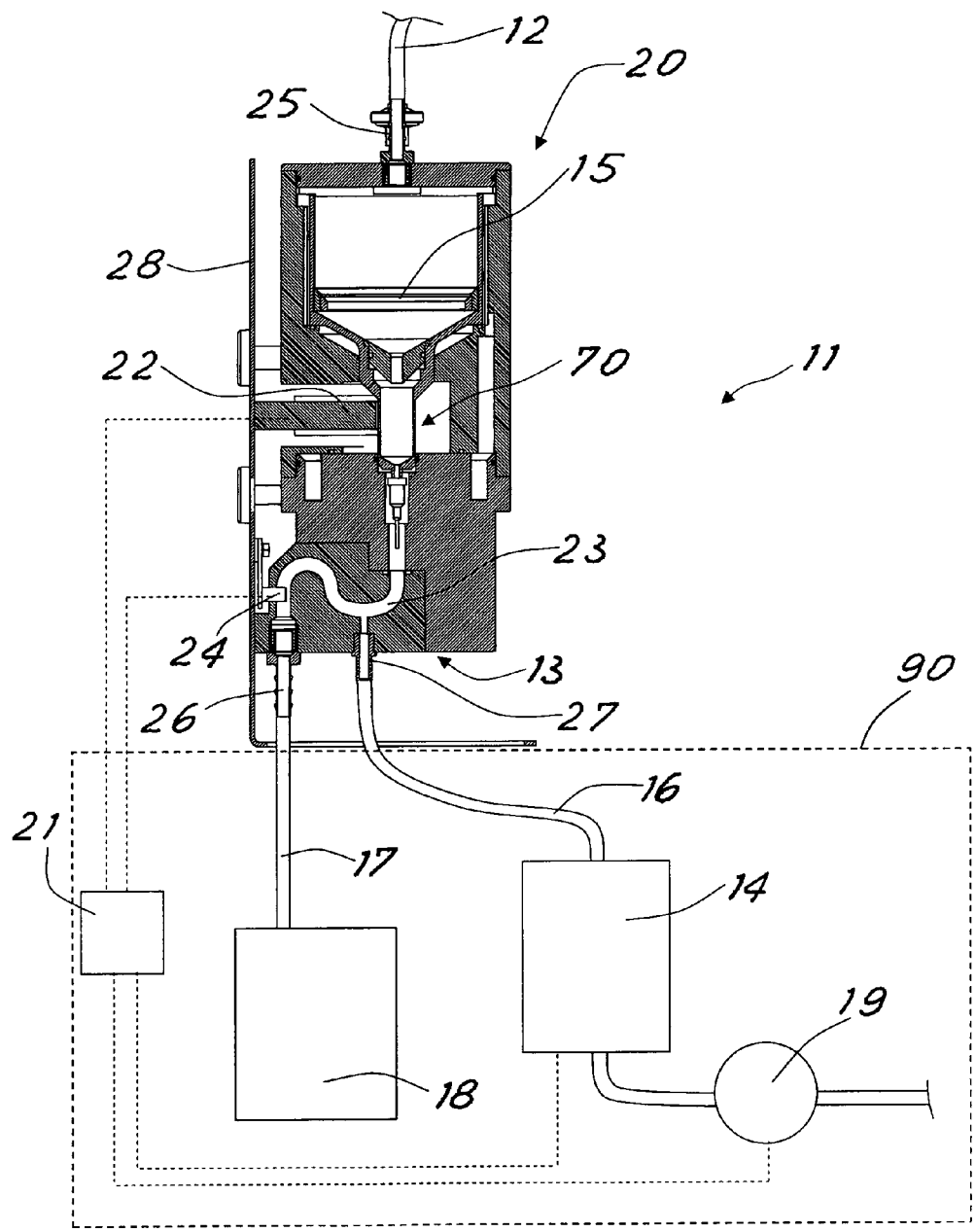
FIG. 1 represents an overall view of the device according to the present invention.

With reference to the figures, FIG. 1 shows a device 11 for the analysis of urine destined for being connected in series to a catheter 12 of a patient's urine, for example a patient admitted to the intensive-care unit of a hospital.

The device comprises means 14 for analyzing a sample of urine and means 13, 19 for feeding a pre-established quantity of urine coming from the catheter 12 to said analysis means.

The device also comprises automatic control means 21 suitable for controlling the feeding of the pre-established quantity of urine to the analysis means 14 and the activation of the latter when the pre-established quantity of urine is supplied thereto.

The means for feeding a pre-established quantity of urine comprise a collection area 23 of the pre-established quantity of urine coming from the catheter and means 19 for transferring the pre-established quantity to the analysis means 14. The collection area advantageously consists of a siphon 23, whereas the means for transferring the known quantity of urine to the cell 14 comprise a pump 19, as described hereunder.

The control means 21, are advantageously configured to effect the transfer of the urine from the collection area 23 to the analysis means 14 provided that a signal is generated from a sensor 24 of the device indicating the filling of the collection portion 23 with the known volume.

The analysis means can comprise an electrochemical measurement cell 14, advantageously capable of effecting analyses on a sample of non-diluted urine. The cell 14 comprises an electrode for pH with a glass membrane, and electrode for sodium with a glass membrane with a high ion selectivity, an electrode for potassium, an electrode for chloride and one for ammonium. The electrodes are superimposed in the central part of the cell so as to form a small channel in which a known volume of urine to be analyzed is introduced. High sensitivity electrodes are advantageously used to also allow the measurement to be made on non-diluted urine. Electrodes of this type are already used in the medical field for other applications and consequently will not be further described herein. Containers of calibrating solutions are associated with the electrochemical cell 14. According to known technology, the calibrating solutions can be brought into the cell at the moment of the measurement using an electro-valve system which can be easily comprehensible to an expert in the field. The means for feeding the urine to the cell 14 are configured so as to supply a known volume of the most recent urine coming from the catheter 12 of the patient. In the preferred embodiment of the invention, the means 13 are suitable for selecting the urine from a flow of urine between the catheter 12 of the patient and a discharge tube 17 of non-analyzed urine, which discharges the urine into a specific bag or container 18 schematically represented in FIG. 1.

The means 13 comprise a portion of U-shaped duct 23 (or siphon), in which the known volume of urine coming from the catheter 12 is collected. The most recent urine is always present in the siphon. The U-shaped portion 23 is at an intermediate height between the catheter 12 and the discharge duct 17 of the non-analyzed urine.

Figure 2:
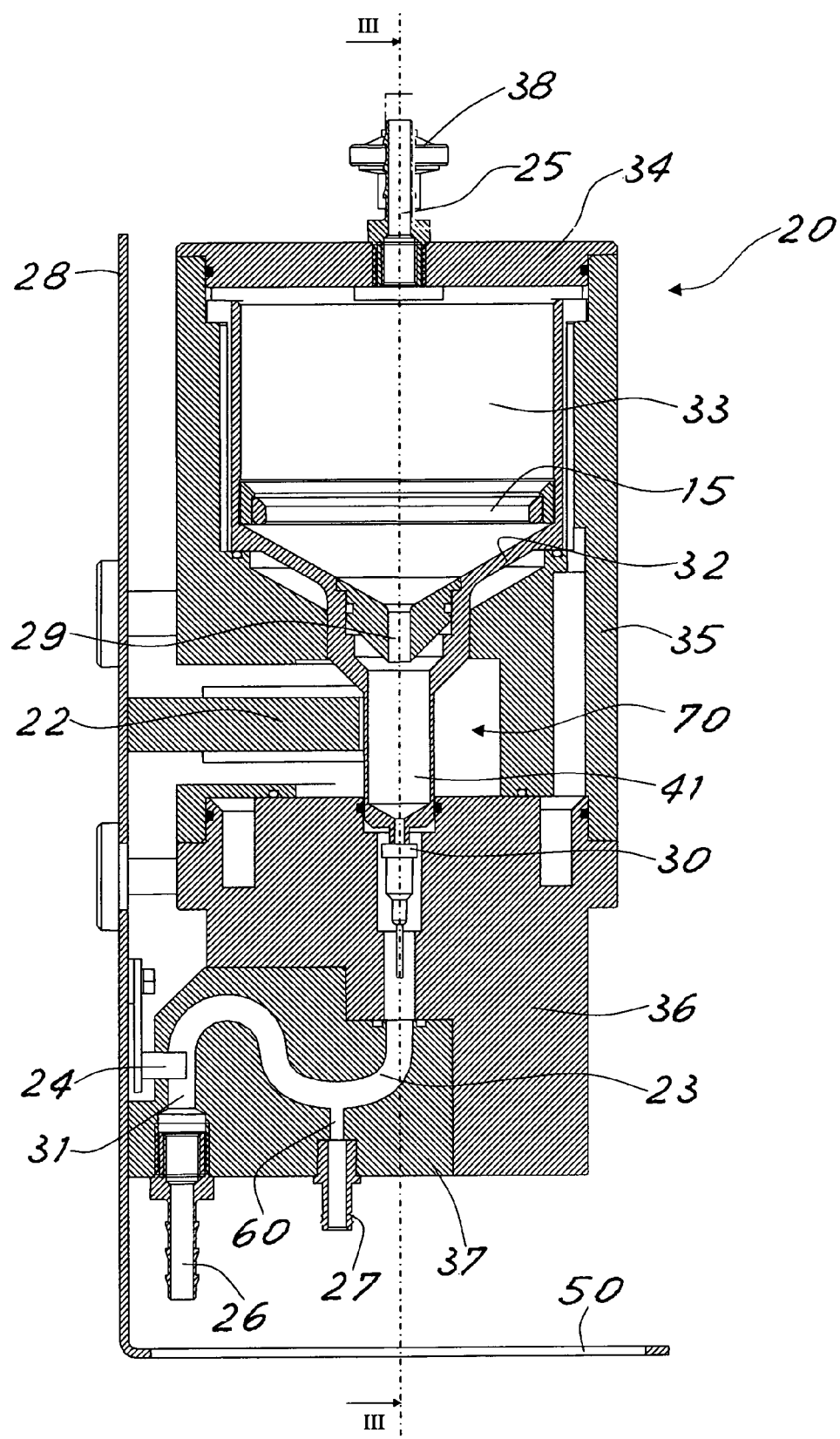
FIG. 2 represents a detailed sectional view of a part of the device.

A passage 60 (see FIG. 2) is formed on the bottom of the U-shaped portion 23, connected to the measurement cell 14 by means of a flexible tube 16.

The passage 60 has a narrow section through which the urine can only pass if sucked downstream of the passage.

For this purpose, there is a pump 19 after the passage 60 which, when activated, transfers the urine collected in the U-shaped portion 23 to the cell 14.

The pump 19 is advantageously situated after the cell 14, connected to a discharge duct of the urine.

The U-shaped portion 23 is made up of a body 20 equipped with two lower connections 26, 27 respectively for discharging the non-analyzed urine and the urine to be sent to the cell 14 by means of the tubes 17 and 16; the body 20 also comprises an upper connection 25 connected to the catheter 12. The discharge connection 26 receives the urine which overflows from the portion 23 through the duct 31.

The device 11 comprises an optical sensor 24 arranged on the portion of duct 31 to provide a signal when the portion 23 is completely filled with urine. The sensor 24, as schematically shown in the figure, is connected to automatic control means 21 of the machine.

The device 11 also comprises means for filtering the urine arriving from the catheter 12, upstream of the means for feeding the known volume to the cell 14. The filtering means comprise a net 15 situated inside a container 33, having an almost cylindrical form above the net 15. The container 33 is assembled inside the body 20 which also houses the U-shaped duct 23. The container 33 receives the urine coming from the catheter 12 through a hole in the lid 34 which closes the top of the internal cavity of the body 20 which houses the container 33. Below the net 15, the container 33 comprises a conical portion (or basin) 32 on whose bottom there is a calibrated passage 29 for the formation of calibrated drops. The calibrated hole 29 can advantageously consist of a separate body with respect to the container 32-33, suitably inserted in the bottom of the conical portion 32.

The device 11 also comprises means 70 for measuring the overall volume of urine coming from the catheter 12, situated in series between the catheter 12 and the U-shaped duct 23.

The means 70 comprise means for dividing the urine into drops and means for counting the drops of urine. As already described, the calibrated passage 29 divides the urine reaching the conical portion 32 of the container 33, into drops. Alternatively, suitable calibrated needles can be used for forming the drops. Below the hole 29 there is a sensor 22 which provides a signal for each drop passing in correspondence with the cavity 41. The walls of the cavity 41 can advantageously form a single piece with the conical portion 32 of the container 33.

The sensor 22, preferably of the optical type, is connected to the control means 21 for providing a signal relating to the passage of the drops. The control means 21 can count the impulses provided by the sensor 22 to keep account of the overall volume of urine produced by the patient within a time unit. Downstream of the sensor 22 there is a further calibrated passage 30 through which the urine reaches the U-shaped collecting portion 23 of the most recent urine. The calibrated passage 30 also determines, together with the hole 29, the size of the drop revealed by the sensor 22.

Furthermore, the narrowing formed by the passage 30 also serves to form an electric decoupling between the electrochemical cell and the catheter of the patient.

The body 20 also comprises a duct 39 which terminates in correspondence with the lower discharge connection 40 (see FIG. 3) to discharge a possible excess of urine which overflows from the container 33.

The body 20 is preferably produced with four pieces 34-37 fixed to each other. The piece 37 forms the U-shaped duct portion 23 and carries the lower connections 26, 27 described above. The piece 36 forms part of the duct 39 and carries the discharge connection 40. The piece 36 also forms a feeding duct of the U-shaped portion 23 and the piece 37 is attached to it from below. The piece 35 forms the upper part of the body with the cavity which houses the container 33.

Figure 3:
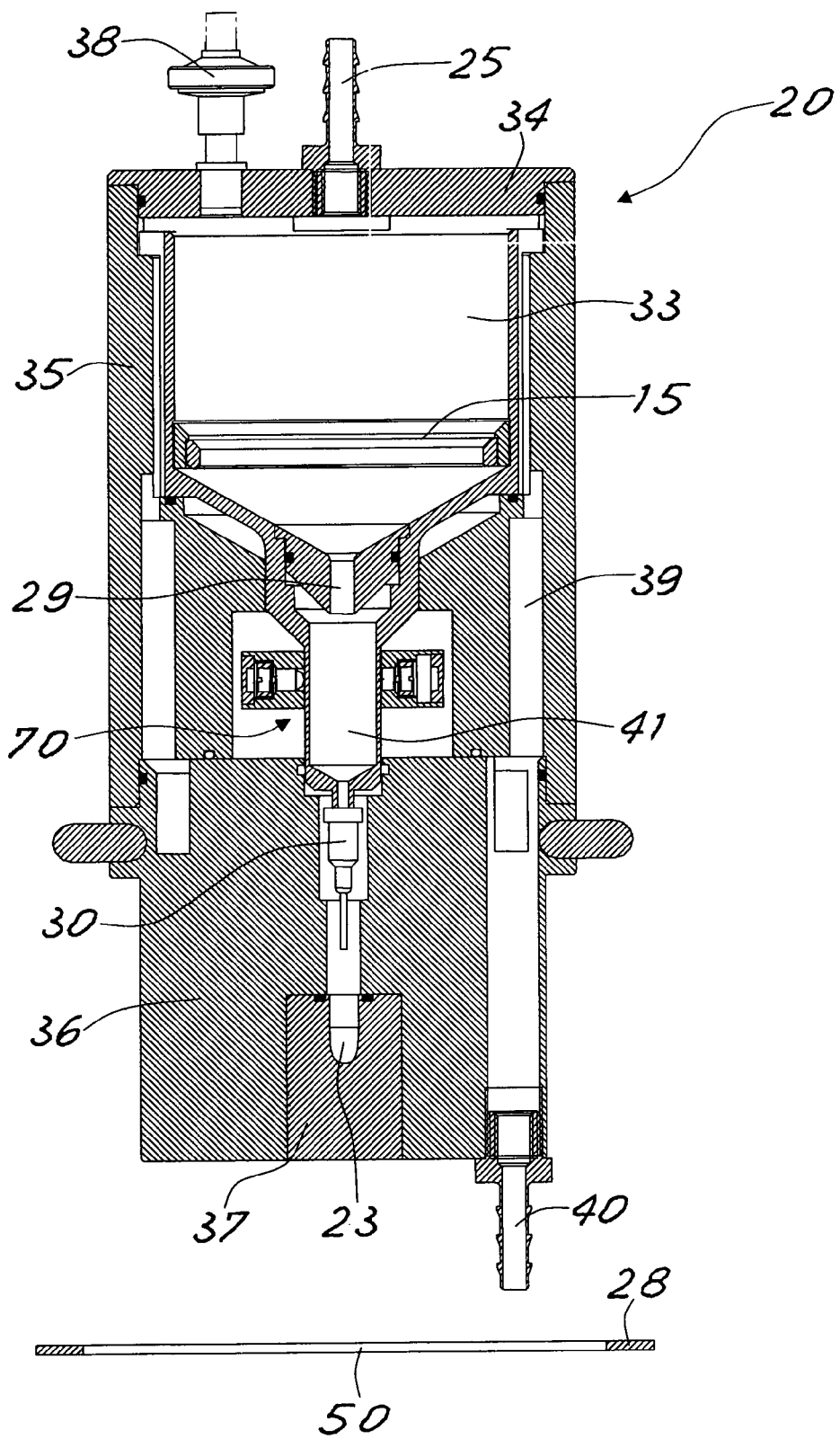
FIG. 3 represents a second sectional view, according to the plane III-Ill shown in FIG. 2.

The piece 35 is closed above by the lid 34 and is assembled on the piece 36. An antibacterial air filter 38, can also be advantageously envisaged on the lid 34, as shown in FIG. 3.

The body 20 is fixed to a rod 28 which keeps it in a vertical position, advantageously at a greater height with respect to the other components of the device (the pump, the electrochemical cell, etc.). The rod 28 can be ensured by an outer case 90 of the device (schematically shown in dashed lines in FIG. 1) which contains the electrochemical cell, the pump, the card which forms the control means and the containers for the calibrating solutions and for the collection of the urine analyzed.

The control means 21 can be produced using any known electronic controller, and advantageously comprise means for memorizing the data supplied by the cell 14 whenever an analysis is performed on a sample of urine sent to the cell.

The control means drive the pump 19 to supply the pre-established quantity of urine also at programmable pre-established time intervals, for example every 30 minutes.

The time interval can naturally vary according to the particular cases and requirements, for example from 10 minutes to 3 hours.

In particular, the controller 21 activates the pump 19 if, at the pre-established time, it has received a signal from the sensor 24 generated by a flow of urine through the duct 31, indicating that the U-shaped portion is filled with a pre-established volume for analysis.

With each measurement cycle, the pump 19 is activated for a period of time or a number of pre-established revs, necessary for transferring the known volume of urine collected into the U-shaped portion 23 inside the cell 14.

Once the pump 19 has sucked the known volume of urine to supply it to the cell 14, the controller 21 activates the start of the clinical-chemical measurement on the sample.

When the electrodes have been stabilized, the results of the measurement are supplied to the controller and memorized.

The controller 21 can be advantageously equipped with a display to visualize the trend with time of the characteristics of the patient's urine, in addition to the quantity of urine within the time unit. The control means can be suitable for processing the data collected, in order to provide complete and integrated physical-chemical results.

Through this direct information, it is possible to process other data useful for the clinical treatment of the patient.

The device according to the invention can be integrated in a wider monitoring system capable of completing the clinical situation of the patient with other information coming from other control systems of other vital organs.

The sensors 22, 24 are advantageously assembled on the body 20 of the device. At this point it is evident how .the objectives of the present invention have been achieved.

In particular, a device is provided which allows the urine produced by a critical patient to be automatically, continuously and directly monitored, not only with respect to the quantity, but also with respect to the physical and chemical characteristics of the urine.

Furthermore, the production of the device is simple and economical, and it has a compact size; this prevents encumbrances from being created around the patient's bed.

The compactness represents an important advantage especially in the case of admittance to the intensive-care unit, where there are already various other machines around the patient's bed.

In addition, the fact that the most recent urine is always analyzed allows there to be a reliable indication of the trend of the chemical characteristics of the urine with time and of the clinical situation of the patient.

The above description of an embodiment applying the innovative principles of the present invention is naturally purely illustrative of said innovative principles and should therefore in no way be considered as limiting the patent scope claimed herein.

What we claim is:

1. A device for the continuous, automated analysis of non-diluted urine configured to be connected in series to a catheter (12) carrying a patient's urine, said device comprising: feeding means (13) imbedded into a body housing (20) connected to the catheter (12) via an upper connection (25) mounted on a hole in the center of a lid (34) which closes the top of a container (33); wherein said upper connection (25) is equipped with an antibacterial air filter (38); said upper connection (25) allowing the patient's urine to flow by gravity from the catheter (12) into the container (33), from which the urine flows through a filter net (15) and through a bottom portion (32) of said container 3(33), wherein said bottom portion (32) is of conical shape, designed to funnel by gravity the urine into a downstream cavity (41) which is connected to:
  means (70) for measuring the overall volume of urine coming from the catheter (12) comprising:
    means (29) for subdividing the urine quantity into calibrated drops by way of a calibrated hole; and
    means (22) for electronically counting the drops of urine passing through the cavity (41) and keeping account of the volume of urine produced by the patient;
  a calibrated passage (30) positioned after said means (22) and positioned downstream of said cavity (41), wherein said calibrated passage is configured to direct the flow of the counted drops into a rigid collection area (23) imbedded into a solid piece (37);
wherein said calibrated passage (30) forms an electric decoupling between said catheter (12) and an analysis means (14) which will receive a pre-established quantity of urine contained inside the collection area (23) for analysis, where the quantity of urine contained in said collecting area (23) is independent of the quantity of urine produced by the patient;
  lower feeding means (19) for transporting the pre-established quantity of urine from the collection are (23) to the analysis means (14) via a lower connection (27);
  a discharge connection (26), connected to said collection area (23), to allow the passage of a non-analyzed urine quantity to a reservoir (18) by way of a discharge duct (17);
  automatic control means (21) for electronically controlling the feeding of the pre-established quantity of urine at programmable, pre-established intervals of time to the analysis means (14); wherein said automatic control means (21) is configured to activate the analysis of urine inside said urine analysis means (14) when the pre-established quantity of urine is inside the collection area (23); and wherein said automatic control means (21) is equipped with a display device configured to display a trend over time of the characteristics of the patient's urine and the quantity of urine produced within a time unit and to produce integrated physical and chemical results to allow a medical staff to formulate a clinical treatment of the patient; wherein said automatic control means (21) is integrated with a monitoring system capable of processing information coming from other control systems monitoring other patients' vital organs;
  an outer case (90) which contains the urine analysis means (14), the lower feeding means (19), the automatic control means (21) and the non-analyzed urine reservoir (18);
  an L shaped rod (28) to which body housing (20) is bolted, to keep it in a vertical position and at a greater height with respect to said outer case (90); wherein said collection area (23) comprises a U-shaped portion connected to an inverted U-shaped portion of the collection area (23) to form a siphon, wherein said U-shaped portion of the ducts collection area (23) collects the portion of the urine to be analyzed, while the excess of the urine is siphoned out, without manual intervention, through the inverted U-shaped portion of the collection area (23) and discharged through the discharge connection (26), without the operation of any mechanical valve;
and wherein said device allows both the quantity and physico-chemical characteristics of the urine produced by the patient to be automatically, continuously, and directly monitored.

2. A device according to claim 1, wherein said control means (21) is configured to perform the transfer of the urine from the collection area (23) to the analysis means (14) only if a signal is generated by an optical sensor (24) of the device which detects the filling up of the collection area (23), which always contains a pre-determined amount of the most recent urine produced by the patient.

3. A device according to claim 2, wherein said optical sensor (24) is positioned inside a portion of a duct (31) downstream of the collection area (23) to provide the control means (21) with a signal when said collection area (23) is full of urine.

4. A device according to claim 1, wherein said U-shaped portion of said collection area (23) has a passage (60) on its lowest part, connected to the analysis means (14) of the urine via the lower connection (27); and wherein said collection area (23) is positioned at an intermediate height between the catheter (12) and a discharge duct (17) to carry non-analyzed urine.

5. A device according to claim 4, wherein said passage (60) has a narrow section through which the urine cannot pass by gravity but it can only pass if sucked by a sub-pressure downstream of the passage, the sub-pressure being caused by lower feeding means (19) and not by gravity alone.

6. A device according to claim 5, wherein said lower means for feeding the urine (19) from the collection area (23) to the analysis means (14) of the urine comprises a pump controlled by the automatic control means (21) which also comprises means for storing the data supplied by the analysis means (14) which is configured to send to a display unit the variation trends with time of the characteristics of the patient's urine and provide integrated physical and chemical results.

7. A device according to claim 6, wherein said pump is activated for a pre-established period of time or activated to turn for a number of pre-established revolutions by the control means (21) for each transfer of urine from the collection area (23) to the analysis means (14).

8. A device according to claim 6, wherein said pump (19) is connected downstream with respect to the analysis means (14) of the urine.

9. A device according to claim 1, wherein said U-shaped portion of the collection area (23) is imbedded into the solid piece (37) equipped with two lower connections (26, 27), connected to the discharge duct (17) for the non-analyzed urine and to a tube (16) connected to the analysis means (14), respectively.

10. A device according to claim 1, wherein said means (70) for measuring the volume of urine is situated in series between the catheter (12) and the feeding means (13) for feeding the urine to the measuring means (14).

11. A device according to claim 1, wherein said analysis means (14) comprises an electrochemical measurement cell.

12. A device according to claim 11, wherein said electrochemical measurement cell is configured to use non-diluted urine and comprises an electrode for measuring pH with a glass membrane and with high ion selectivity, and electrodes for measuring sodium, potassium, chloride and ammonium, respectively; wherein said electrodes are superimposed in the central part of said electrochemical measurement cell so as to form a small channel in which the pre-established quantity of urine to be analyzed is introduced.

* * * * *